(12) United States Patent
Cormier et al.

(10) Patent No.: US 9,918,661 B2
(45) Date of Patent: Mar. 20, 2018

(54) ALVEOLAR BREATH COLLECTION APPARATUS

(71) Applicant: Picomole Instruments Inc., Edmonton (CA)

(72) Inventors: John Cormier, Dieppe (CA); Chris Purves, Moncton (CA); Jacques Vautour, Dieppe (CA); Denis Dufour, Montreal (CA)

(73) Assignee: Picomole Instruments, Inc., Edmonton (CA)

( * ) Notice: Subject to any disclaimer, the term of this patent is extended or adjusted under 35 U.S.C. 154(b) by 159 days.

(21) Appl. No.: 14/720,456

(22) Filed: May 22, 2015

(65) Prior Publication Data

US 2015/0335267 A1 Nov. 26, 2015

Related U.S. Application Data

(60) Provisional application No. 62/002,159, filed on May 22, 2014.

(51) Int. Cl.
*A61B 5/08* (2006.01)
*A61B 5/083* (2006.01)
(Continued)

(52) U.S. Cl.
CPC ............ *A61B 5/082* (2013.01); *A61B 5/0836* (2013.01); *A61B 5/097* (2013.01); *B01D 53/02* (2013.01);
(Continued)

(58) Field of Classification Search
CPC ....... A61B 5/082; A61B 5/0836; A61B 5/097; B01D 53/0415; B01D 53/0407;
(Continued)

(56) References Cited

U.S. PATENT DOCUMENTS 5,465,728 A 11/1995 Phillips
6,582,376 B2 6/2003 Baghdassarian
(Continued)

OTHER PUBLICATIONS

The English language translation of the foreign priority document of US 2016/0174875, DE 102013215640, is attached.*
(Continued)

*Primary Examiner* — Christian Jang
*Assistant Examiner* — Andrey Shostak
(74) *Attorney, Agent, or Firm* — Marsh Fischmann & Breyfogle LLP; Jonathon A. Szumny

(57) ABSTRACT

An apparatus for collecting volatile compounds in human breath. The apparatus includes a device for discriminating between alveolar and non-alveolar portions of exhaled breath, a device for measuring volume of exhaled breath, a chamber with a piston or similar compressible device with clean internal services designed to collect a precise volume of alveolar breath, a pump to draw the exhaled breath from the chamber through at least one sorbent tube, a subsystem for introducing a clean gas into the chamber to expand it and for purging the tubing of the system, and a subsystem for selectively collecting a room air sample. A manifold is provided in the apparatus for receiving sorbent tubes and comprises an input block and output block, and a locking lever for actuating the input and output blocks linearly towards and away from each other and selectively locking them in a fully closed position.

8 Claims, 3 Drawing Sheets

(51) Int. Cl.
B01D 53/04 (2006.01)
B01D 53/02 (2006.01)
A61B 5/097 (2006.01)

(52) U.S. Cl.
CPC ...... *B01D 53/0407* (2013.01); *B01D 53/0415* (2013.01); *B01D 53/0423* (2013.01); *B01D 2259/4533* (2013.01); *G01N 2291/0256* (2013.01)

(58) Field of Classification Search
CPC ................ B01D 53/0423; B01D 53/02; B01D 2259/4533; G01N 2291/0256
See application file for complete search history.

(56) References Cited

U.S. PATENT DOCUMENTS

| | | |
|---|---|---|
| 6,726,637 B2 | 4/2004 | Phillips |
| 8,288,727 B2 | 10/2012 | Cormier et al. |
| 2003/0109794 A1* | 6/2003 | Phillips .................. A61B 5/097 600/543 |
| 2004/0162500 A1 | 8/2004 | Kline |
| 2005/0177056 A1* | 8/2005 | Giron ...................... A61B 5/097 600/543 |
| 2008/0139021 A1* | 6/2008 | Suzuki .................. G01R 1/0416 439/92 |
| 2012/0266883 A1* | 10/2012 | Taylor .................... A61M 16/10 128/205.12 |
| 2015/0032019 A1* | 1/2015 | Acker .................... A61B 5/082 600/532 |
| 2016/0174875 A1* | 6/2016 | Forster .................. A61B 10/00 600/543 |

OTHER PUBLICATIONS

Cope, et al., "Effects of ventilation on the collection of exhaled breath in humans", J App I Physiol 96: 1371-1379, 2004.

\* cited by examiner

ALVEOLAR BREATH COLLECTION APPARATUS

CROSS-REFERENCE TO RELATED APPLICATION

This application claims priority to U.S. Provisional Patent Application Ser. No. 62/002,159, filed on May 22, 2014, entitled "ALVEOLAR BREATH COLLECTION APPARATUS", the contents of which are incorporated herein by reference.

FIELD OF THE INVENTION

The following relates generally to the field of medical diagnostics, and more particularly to collection of volatile breath compounds for analysis.

BACKGROUND OF THE INVENTION

The analysis of volatile organic compounds (VOCs) in exhaled human breath is rapidly emerging as a painless, non-invasive alternative to conventional methods of disease diagnosis and metabolite measurement. Breath VOC measurement is also commonly used for monitoring the effects of human exposure to environmental pollutants and drugs.

Hundreds of VOCs have been found in exhaled human breath, many of which originate from blood-air exchange in the lower (i.e. alveolar) area of the lungs. Because these compounds are mostly present at very small concentrations (parts-per-billion or less), their measurement by instruments such as GC-MS (Gas Chromatography-Mass Spectrometer) or infrared cavity-enhanced technologies often requires pre-concentration by filtering out undesired compounds such as nitrogen ($N_2$) and oxygen ($O_2$). The relatively large quantities of water vapour and carbon dioxide ($CO_2$) present in exhaled breath should also be filtered out since they can hinder measurement of remaining VOCs in instruments such as GC-MS and IR spectrometers.

U.S. Pat. No. 5,465,728 to Philips discloses an Apparatus which is used to collect mammalian breath for chemical analysis and as a diagnostic tool for the physician. The Apparatus comprises a fluid reservoir container having first and second ends and a body extending between these ends so as to define an interior chamber; a breath entry portal; a breath exit portal; a sampling portal; a jacket to maintain the temperature of the chamber; a sample container for holding samples of exhaled breath; and pump means for moving selected samples of breath from the reservoir container into the sample container.

U.S. Pat. No. 6,726,637 also to Philips discloses an arrangement for the collection, concentration, and optional analysis of volatile organic components in alveolar breath that includes a condensation unit which removes water vapor from the alveolar breath. The arrangement has two significant shortcomings. The first is that the disclosed method for alveolar sampling is based on assumptions of the subject's lung capacity and expiration rate. The method is therefore subject to inaccuracies in cases where a particular subject's lung capacity and/or expiration rate deviates strongly from the normal assumptions. Furthermore, there is no discussion about how cross-contamination of VOCs between subjects is prevented or otherwise dealt with.

U.S. Pat. No. 6,582,376 to Baghdassarian discloses a device for collecting alveolar breath. Breath is expired into the inlet of a hollow body. The hollow body has two outlets, with a valve disposed in each outlet. The concentration of a specific gaseous component of expired breath is monitored by a gas concentration monitor as the expired breath passes through the hollow body to determine when alveolar breath is present in the hollow body. When alveolar breath is present in the hollow body, the valve in the second outlet is actuated to an open position to collect the alveolar breath in the collection reservoir affixed to the hollow body at the second outlet. While the Baghdassarian Apparatus employs a $CO_2$-based method for discriminating between alveolar and tidal breath, it is unable to concentrate VOCs and is unable to remove undesired $CO_2$ and water from the breath sample.

United States Patent Application Publication No. 2004/0162500 to Kline discloses a diagnosis method for respiratory disease based on the separation of the expired airway phase in an exhaled breath from the alveolar phase, and a device to accomplish the method. The device includes a cartridge assembly and a disposable condensing chamber carried in a substantially enclosed housing. The cartridge assembly includes a disposable cartridge and a reusable control system that monitors a characteristic of gas passing through the cartridge to determine when to divert the exhaled breath to an exhaust outlet and when to divert the exhaled breath to the condensing chamber. The characteristic is selected as being representative of the transition from the expired airway phase to the alveolar phase. Also included are a refrigeration system, an auxiliary monitoring system for determining when a sufficient volume of gas has been produced, and a built-in analyzer.

The Kline device contains a mechanism capable of diverting the non-alveolar component of breath from being collected and concentrated, based on the measurement of some characteristic of the exhaled breath passing through. However, the Kline Apparatus is designed to collect breath water vapour for subsequent analysis of the breath condensates found therein, and is not appropriate for applications where it is desirable to filter out such water and to concentrate remaining breath VOCs.

SUMMARY OF THE INVENTION

It is an object of an aspect of the invention to provide a breath collection Apparatus capable of capturing an alveolar breath sample and facilitating delivery of the VOCs collected from said sample to an appropriate instrument for high-accuracy multi-compound analysis. The breath collection Apparatus preferably has the following capabilities: 1. Ability to pre-concentrat VOCs; 2. Ability to accurately sample the alveolar component of exhaled breath; 3. Ability to filter out $N_2$, $O_2$, $H_2O$ and $CO_2$; 4. Ability to prevent VOC cross-contamination from previous collections, so as to properly handle multiple samples; 5. An infection control mechanism; 6. Portable and easy to use; 7. Ability to collect room air VOCs, for baseline measurements.

In accordance with an aspect, there is provided an Apparatus for collecting volatile compounds in human breath comprising a device for discriminating between alveolar and non-alveolar portions of exhaled breath by real-time measurement of a physical characteristic of said exhaled breath; a device for measuring volume of exhaled breath; a chamber with piston or similar compressible device with clean internal surfaces designed to collect a precise volume of the alveolar portion of the exhaled breath; a pump to draw the exhaled breath collected in the chamber through at least one sorbent tube; a subsystem for introducing a clean compressed gas into the chamber to expand it, and for purging the internal tubing of the system; and a subsystem for selectively collecting a room air sample.

In a preferred embodiment, the physical characteristic is concentration of $CO_2$ in the breath sample.

According to another aspect, there is provided a manifold for receiving at least one sorbent tube, the manifold comprising an input block having at least one open-topped channel for receiving an input end of a sorbent tube, and an input port within the open-topped channel configured to be in fluid communication with an input end of the sorbent tube; an output block having at least one open-topped channel for receiving an output end of a sorbent tube, and an output port configured to be in fluid communication with an output end of the sorbent tube; and a locking lever associated with at least one of the input and output blocks for moving the input and output blocks linearly towards and away from each other between fully open and closed positions.

BRIEF DESCRIPTION OF THE DRAWINGS

Embodiments of the invention will now be described with reference to the appended drawings in which.

DETAILED DESCRIPTION

Figure 1:
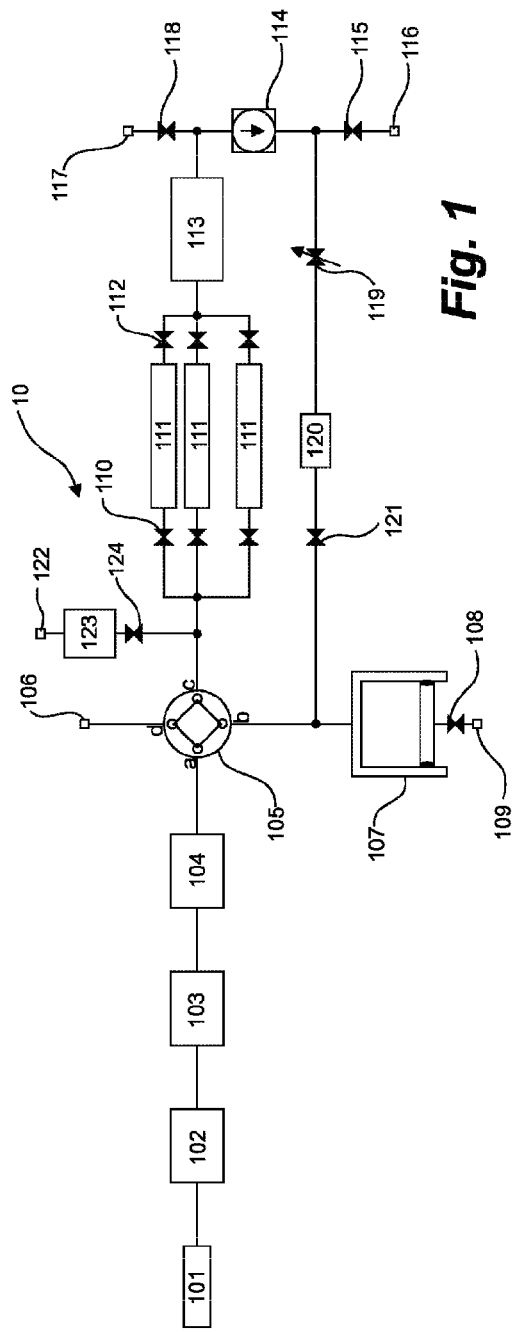
FIG. 1 is a block diagram of components of a breath collection apparatus, according to an embodiment.

FIG. 1 is a block diagram of components of a breath collection Apparatus 10, according to an embodiment. Apparatus 10 incorporates features that provide the seven previously-described capabilities. In particular, Apparatus 10 is designed to collect a precise volume of alveolar air from a subject 101 and to deliver this sample onto one or a plurality of sorbent tubes 111. The sorbent tubes 111, by design, filter out undesired nitrogen (N2), oxygen (O2), water (H2O) and carbon dioxide (CO2). As will be described, Apparatus 10 further provides the ability to concentrate the sample by multiple breath exhalations if desired or needed for testing.

In one embodiment, after collection the sorbent tubes 111 can be removed and brought to an appropriate instrument for analysis. An instrument suitable for receiving samples from such sorbent tubes after collection and conducting appropriate analyses of the concentrations of VOCs is disclosed in U.S. Pat. No. 8,288,727 to Cormier et al., the contents of which are incorporated herein by reference in their entirety.

Turning to FIG. 1, Apparatus 10 contains a mouthpiece 102 fitted with a disposable microbial filter into which the subject exhales. A flow meter 103 allows for the measurement of breath volume during the exhalation process. A device 104 for receiving exhaled breath and for discriminating between alveolar and non-alveolar portions of the exhaled breath by real-time measurement of a physical characteristic of said exhaled breath is provided. In this embodiment, the device 104 is a capnometer, such that the physical characteristic is concentration of $CO_2$.

This $CO_2$-based technique of discriminating between alveolar and non-alveolar breath has been shown to be accurate and to allow for a robust normalization of breath VOCs. More information about the $CO_2$-based method may be found in Cope et al., *Effects of ventilation on the collection of exhaled breath in humans, J Appl Physiol* 96: 1371-1379, 2004.

Pursuant in the breath flow path to the capnometer 104, a 4-way valve 105 is provided. 4-way valve 105 provides fluid communication between selected ones of the capnometer 104 at port a, a collection chamber 107 having a piston and an exhaust port 109 via valve 108 at port b as well as a filter in fluid communication with both port b via valve 121 and a pump 114 via valve 119, various components via respective on/off valves 124, 110 and 112 at port c, and an exhaust outlet 106 at port d.

The various components pursuant to port c of 4-way valve 105 include sorbent tubes 111 with input ends in fluid communication with respective input valves 110. Sorbent tubes 111 are also in fluid communication with respective output valves 112, which are each in turn in fluid communication with a flow controller 113. Flow controller 113 is in fluid communication with pump 114, and pump 114 is in fluid communication with each of clean gas inlet 117 via respective valve 118, and gas exhaust 116 via respective valve 115.

The various components pursuant to port c of 4-way valve 105 also include an ambient air inlet 122 via a dust filter 123, for enabling an operator of Apparatus 10 to collect VOCs in ambient air while collecting breath samples. This is useful in determining if the VOCs measured in exhaled breath are produced endogenously or are result from the inhalation of ambient air.

Figure 2:
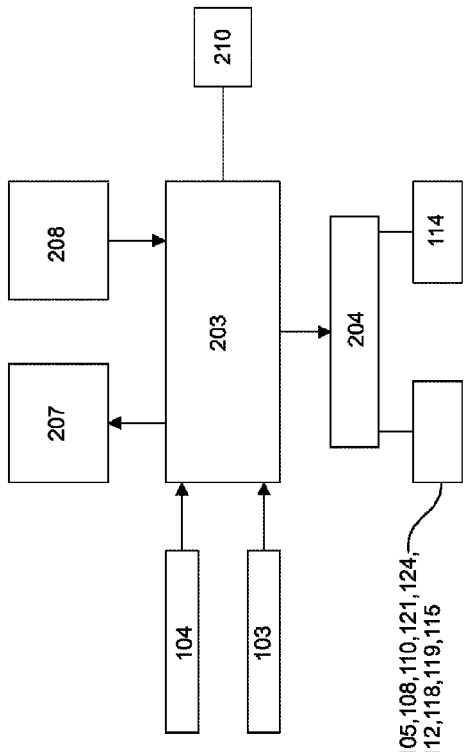
FIG. 2 is a schematic diagram of components of the breath collection Apparatus of FIG. 1, in communication with a microprocessor.

As shown in the schematic diagram of FIG. 2, the valves 105, 108, 110, 121, 124, 112, 118, 119, 115 inside the Apparatus 10 are controlled by a Microprocessor 203 via a relay array 204. Pump 114 is also controlled by Microprocessor 203 via relay array 204.

Microprocessor 203 is capable of executing computer readable program code stored on a computer readable medium 210. Computer readable medium may include a main memory, such as a random access memory (RAM) or other dynamic storage device (e.g., dynamic RAM (DRAM), static RAM (SRAM), and synchronous DRAM (SDRAM)), in communication with Microprocessor 203 for storing information and instructions to be executed by Microprocessor 203. The main memory may be used for storing temporary variables or other intermediate information during the execution of instructions by the Microprocessor 203. Microprocessor 203 may include memory structures such as registers for storing such temporary variables or other intermediate information during execution of instructions. Apparatus 10 further includes a read only memory (ROM) or other static storage device (e.g., programmable ROM (PROM), erasable PROM (EPROM), and electrically erasable PROM (EEPROM)) in communication with Microprocessor 203 via a bus or other communications structure for storing static information and instructions for the microprocessor.

Also in communication with Microprocessor 203 is a user interface display 207 for displaying Apparatus status information and a simple touch-button interface 208 for control by an operator of Apparatus 10. The Apparatus has an access door through which the sorbent tubes can be easily removed following sample collection, to be replaced with conditioned tubes prior to the next sample collection.

Figure 3A:
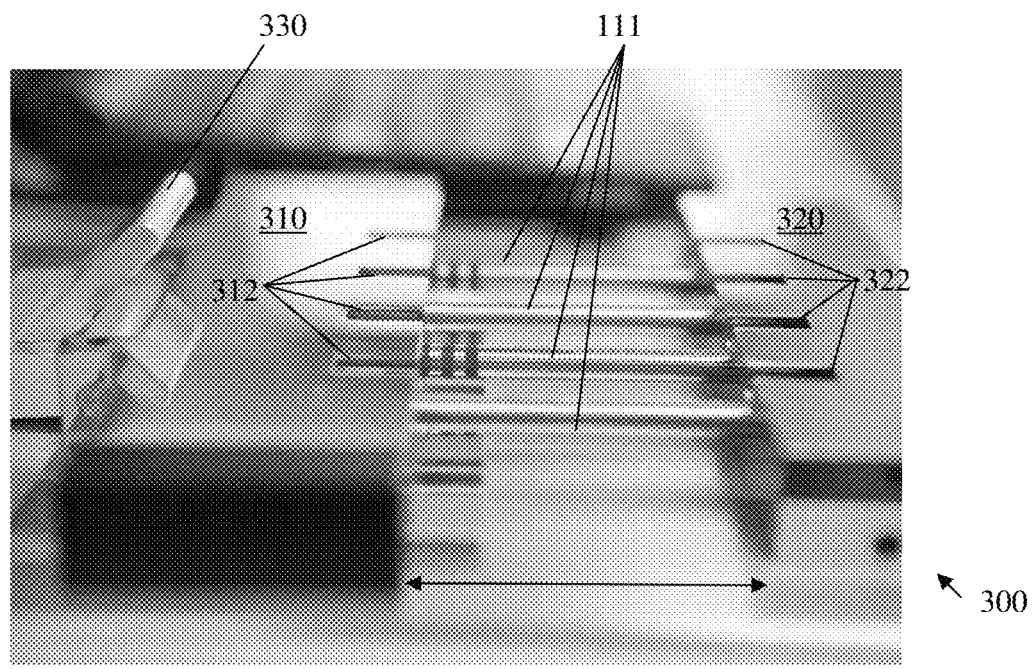
FIG. 3A is a side perspective view of a manifold for receiving and releasably securing a plurality of sorbent tubes in fluid communication with the apparatus.
Figure 3B:
FIG. 3B is a side perspective view of a container containing a plurality of sorbent tubes suitable for securing in the manifold of FIG. 3A.

FIG. 3A is a side perspective view of a manifold 300 that, in this embodiment, is positioned at the top of a breath collection Apparatus for receiving and releasably securing one or a plurality of sorbent tubes 111, such as the sorbent tubes 111 shown in FIG. 3A, in fluid communication with the apparatus. The manifold 300 has an input block 310, an output block 320, and a locking lever 330. The input and output blocks 310, 320 are manually linearly moveable towards each other to a closed position, and away from each other to a fully open position. In this embodiment, the locking lever 330 is mechanically coupled to the input block 310 to linearly move the input block 310 towards and away from the output block 320, which remains fixed in position, and to selectively lock the input block 310 in the closed position.

The input block 310 includes a plurality of open-topped channels 312 into which an input end of a sorbent tube 111 may be placed by a person administering collection of breath samples. Each of the channels 312 of the input block 310 is in fluid communication with an input port (not shown), which is in turn in fluid communication with a respective input valve 110.

In a similar manner, the output block 320 includes a plurality of open-topped channels 322 into which an output end of a sorbent tube may be placed. Each of the open-topped channels 322 of the output block 320 is aligned with a corresponding open-topped channel 312 in the input block 310. Each of the open-topped channels 322 of the output block 320 is in fluid communication with an output port (not shown), which is in turn in fluid communication with a respective output valve 112.

The range of linear movement of the input and output blocks 310, 320 with respect to each other is preferably small enough that, in the fully open position, sorbent tubes 111 can still be set into and be supported at their ends by the respective aligned open topped channels 312, 322 of the input and output blocks 310, 320. Prior to attempting collection of a breath sample, with the one or more sorbent tubes 111 supported in respective open-topped channels 312, 322, the locking lever 330 is pivoted to bring the input and output blocks 310, 320 towards the closed position. As the input and output blocks 310, 320 are brought together, all of the sorbent tubes 111 are caused to contact and be sealed in fluid communication with respective input and output ports of the input and output blocks 310, 320. At this position, the locking lever can be put into its locked position, so that the sorbent tubes 111 remain affixed in place until such time as the locking lever 330 is moved to an unlocked position.

Operation of the Apparatus 10 will now be described. With one or more fresh sorbent tubes 111 having been placed and locked into manifold 300 by an operator, the breath collection Apparatus is ready for operation. The operator activates the instruction set of the breath collection Apparatus 10 via the touch-button interface 208, and Apparatus 10 in turn displays instructions for a subject via user display 207. The subject approaches the mouthpiece 102, draws a breath, and exhales into the mouthpiece 102. During the first part of the exhalation, which typically will comprise non-alveolar breath, the breath is conveyed through a 4-way valve and vented out of the instrument via the exhaust 106. Once the capnometer 104 detects that the CO2 in the breath passing through has reached the appropriate threshold level indicating alveolar breath, the Microprocessor 203 responds by signalling the relay array 206 to in turn adjust the positioning of the 4-way valve 205 thereby to convey the remainder of the incoming breath exhalation into the collection chamber 107 associated with the piston.

Advantageously, if it is detected that an insufficient volume of alveolar breath has been collected in the collection chamber 107 after the initial breath, the Microprocessor 203 will cause user display 207 to instruct the subject to exhale again into the mouthpiece 102. In the interim, the 4-way valve is positioned to keep the already-collected breath within collection chamber 107. Upon exhaling for the second (or third etc.) time, the non-alveolar portion of the breath will again be vented by operation of the 4-way valve 205 until alveolar breath is detected by the capnometer 104, at which point the Microprocessor 203 again will signal the relay array 206 to adjust the positioning of the 4-way valve 205 thereby to convey the remainder of the incoming breath exhalation into the collection chamber 107.

Once it has been determined that enough breath has been collected in the collection chamber 107, the subject can stop providing breath samples. The Microprocessor 203 signals the relay array 204 to activate a pump 114 thereby to draw the captured breath from the collection chamber 107 through a selected one or more sorbent tubes 111 via respectively opened valves 110 and 112. The pump 114 induces a vacuum in the collection chamber 107, causing the piston to compress as the breath sample is drawn out of the collection chamber 107 towards and into the one or more sorbent tubes 111. The sorbent tubes 111 respectively contain sorbent materials such as Chromosorb® or Tenax® which allow small molecules such as water (H2O) and CO2 to pass through while adsorbing the remaining larger VOCs of interest. Each sorbent tube 111 through which a breath sample is being drawn by pump 114 may incorporate a different material for adsorbing different VOCs. Once the piston has reached its full compression position, the breath sample has been fully adsorbed into the one or more sorbent tubes 111 and the sample has thereby been collected. At this point, the Microprocessor 203 signals the relay array 204 to deactivate the pump 114.

It is desirable to cleanse the various fluid lines, the collection chamber 107 including the piston, the various valves and the other components of Apparatus 10 of trace VOCs remaining within, so that subsequent samples may be collected from the same subject or from another subject. In order to achieve cleansing, a source of pressurized clean air is provided via inlet 117, and is pressurized either (1) internally by running the pump 114 to draw filtered room air, or (2) externally via a compressed gas cylinder (not shown). The pressurized clean air is used to expand and clean the piston and collection chamber 107, and dry out any possible water condensation and other moisture from Apparatus 10. Once this has been done, Apparatus 10 is ready to collect another sample without significant risk of cross-contamination.

Figure 4:
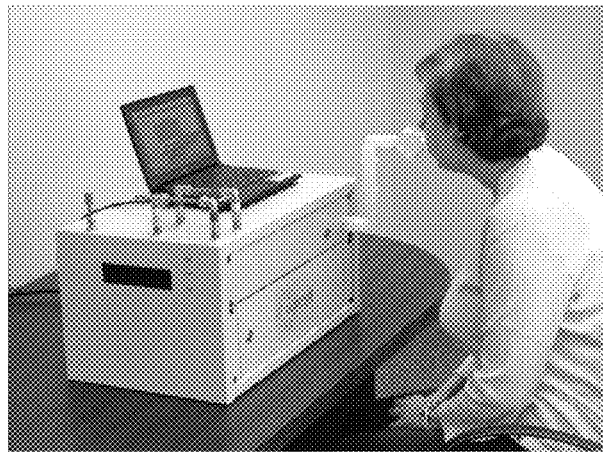
FIG. 4 is a side perspective view of the outside of a breath collection Apparatus in use, according to an embodiment.
Figure 5:
FIG. 5 is a front perspective view of the outside of a breath collection apparatus, according to an alternative embodiment.

FIG. 4 is a side perspective view of the outside of a breath collection Apparatus in use by a subject, according to an alternative embodiment, and FIG. 5 is a front perspective view of the outside of a breath collection Apparatus according to another alternative embodiment.

Although embodiments have been described with reference to the drawings, those of skill in the art will appreciate that variations and modifications may be made without departing from the spirit, scope and purpose of the invention as defined by the appended claims.

For example, in an alternate embodiment, sorbent tube heaters are associated with the sorbent tubes 111, and additional input and output ports are introduced, allowing for desorption of sorbent tube samples directly into a VOC measurement instrument, rather than removal of sorbent tubes for insertion into an analysis device after each sample is collected. In this configuration, the sorbent tubes 111 can then be conditioned by heating and purging and prepared for the next sample collection, without having to remove the sorbent tubes 111.

What is claimed is:

1. An apparatus for collecting volatile compounds in human breath comprising:
   (a) a device for discriminating between alveolar and non-alveolar portions of exhaled breath by real-time measurement of a physical characteristic of the exhaled breath;
   (b) a device for measuring volume of the exhaled breath;
   (c) a chamber with a piston with internal surfaces designed to collect a precise volume of the alveolar portion of the exhaled breath;
   (d) a pump to draw the exhaled breath collected in the chamber through at least one sorbent tube;
   (e) a subsystem for introducing a clean compressed gas into the chamber to expand it, and for purging internal tubing of the subsystem;
   (f) a subsystem for selectively collecting a room air sample;
   (g) a multi-way valve for directing the exhaled breath; and
   (h) a manifold for receiving the at least one sorbent tube, the manifold comprising:
      (1) an input block having at least one open-topped channel for receiving an input end of the at least one sorbent tube, and a first input port within the open-topped channel configured to be in fluid communication with the input end of the at least one sorbent tube;
      (2) an output block having at least one open-topped channel for receiving an output end of the at least one sorbent tube, and a first output port configured to be in fluid communication with the output end of the at least one sorbent tube; and
      (3) a locking lever associated with at least one of the input and output blocks for moving the input and output blocks linearly towards and away from each other between fully open and closed positions, wherein the locking lever is configured to selectively lock the input and output blocks in the closed position such that the locking lever fluidically seals the at least one sorbent tube with the first input and output ports of the respective input and output blocks.

2. The apparatus of claim 1, wherein the physical characteristic of the exhaled breath is the concentration of $CO_2$.

3. The apparatus of claim 2, comprising:
   (i) at least one heater associated with the at least one sorbent tube; and
   (j) a second input port and a second output port associated with the at least one sorbent tube to convey breath samples to the at least one sorbent tube and to convey volatile compounds during desorption of the at least one sorbent tube to a volatile compound measurement instrument.

4. The apparatus of claim 3, comprising:
   (k) a gas port for conveying compressed gas into the apparatus for chamber expansion and line purging.

5. The apparatus of claim 2, comprising:
   (i) a gas port for conveying compressed gas into the apparatus for chamber expansion and line purging.

6. The apparatus of claim 1, wherein in the fully open position the distance between the open-topped channels of the input block and the open-topped channels of the output block corresponds generally to the length of the at least one sorbent tube.

7. The apparatus of claim 1, comprising:
   (i) at least one heater associated with the at least one sorbent tube; and
   (j) a second input port and a second output port associated with the at least one sorbent tube to convey breath samples to the at least one sorbent tube and to convey volatile compounds during desorption of the at least one sorbent tube to a volatile compound measurement instrument.

8. The apparatus of claim 1, comprising:
   (i) a gas port for conveying compressed gas into the apparatus for chamber expansion and line purging.

* * * * *